(12) United States Patent
Canty et al.

(10) Patent No.: US 7,193,702 B2
(45) Date of Patent: Mar. 20, 2007

(54) INSERTION FLUID INSPECTION DEVICE

(75) Inventors: Thomas M. Canty, Williamsville, NY (US); Paul J. O'Brien, East Aurora, NY (US)

(73) Assignee: J.M. Canty Inc., Buffalo, NY (US)

( * ) Notice: Subject to any disclaimer, the term of this patent is extended or adjusted under 35 U.S.C. 154(b) by 418 days.

(21) Appl. No.: 10/895,874

(22) Filed: Jul. 21, 2004

(65) Prior Publication Data

US 2006/0017930 A1    Jan. 26, 2006

(51) Int. Cl.
*G01N 21/01*    (2006.01)
*G01N 1/10*    (2006.01)
*G01N 21/00*    (2006.01)

(52) U.S. Cl. .................. 356/244; 356/246; 356/440

(58) Field of Classification Search ........... 356/244, 356/246
See application file for complete search history.

(56) References Cited

U.S. PATENT DOCUMENTS

| 2,744,487 | A | 5/1956 | Moore et al. ............. 116/117 |
| 3,299,851 | A | 1/1967 | Olsen ....................... 116/117 |
| 3,770,342 | A | 11/1973 | Dudragne .................... 351/7 |
| 3,837,226 | A | 9/1974 | Kawawa ..................... 73/331 |
| 4,245,566 | A | 1/1981 | Shimansky et al. ......... 109/49.5 |
| 4,736,734 | A | 4/1988 | Matsuura et al. ............ 128/6 |
| 4,746,178 | A | 5/1988 | Canty ....................... 350/96.1 |
| 5,202,758 | A | 4/1993 | Tamburrino .................. 358/98 |
| 5,230,556 | A | 7/1993 | Canty et al. ................ 362/32 |
| 5,604,532 | A | 2/1997 | Tillmanns .................... 348/84 |
| 5,730,701 | A | 3/1998 | Furukawa et al. ........... 600/127 |
| 6,259,523 | B1 * | 7/2001 | Welker ..................... 356/241.1 |
| 6,450,655 | B1 | 9/2002 | Walck et al. ................. 362/3 |
| 2003/0103756 | A1 | 6/2003 | Canty et al. ............... 385/138 |

FOREIGN PATENT DOCUMENTS

DE   200 03 712    7/2000
EP   0 343 558    11/1989

OTHER PUBLICATIONS

International Search Report for EP 05 01 5505 (3 pages).

* cited by examiner

*Primary Examiner*—Gregory J. Toatley, Jr.
*Assistant Examiner*—Amanda Merlino
(74) *Attorney, Agent, or Firm*—Darby & Darby

(57) ABSTRACT

A fluid inspection device for inspecting a fluid in a vessel includes an elongate insertion well having a rear end disposed at the wall of the vessel and a front end disposed in the interior of the vessel. An inside of the insertion well is sealed off from the fluid in the vessel and an outside of the insertion well is in contact with the fluid in the vessel. A camera unit is disposed in the inside of the insertion well, and a lens in operative communication with the camera unit is disposed at the front end of the insertion well so that a front end of the lens is in contact with the fluid and a rear end of the lens is inside the insertion well. In addition, a light guide having a light emitting end is configured to guide light from the inside of the insertion well to the light emitting end. The light emitting end is disposed forward of the front end of the lens and directs the light at an angle toward the front end of the lens, and a gap between the front end of the lens and the light emitting end is capable of receiving the fluid.

22 Claims, 3 Drawing Sheets

INSERTION FLUID INSPECTION DEVICE

The present invention relates to a fluid inspection device for inspecting a fluid in a vessel, and more particularly to a fluid inspection system having an insertion well extending into an interior of the vessel. The present invention also provides a method for inspecting a fluid in a vessel.

BACKGROUND

Many industrial processes, such as various manufacturing and chemical processes take place within closed or partially closed containers or vessels, making accurate observation of those industrial processes more difficult. Accurate observation of the processes within such vessels is desirable, for example, to enable improved control and/or industrial efficiency. This is especially true where removal of product for inspection is not possible or practical, or where removal of the product would lead to inaccurate results due to the loss of process conditions.

It is known to use various devices for directly or remotely viewing the interior of a vessel, such as a pressure vessel, reaction vessel, process pipeline, or the like. A simple device for this purpose is a transparent viewing window provided in a wall of the vessel or pipeline. By looking through this window, an operator can observe liquid levels, color changes, and other visually determinable factors taking place within the vessel. Several of these viewing windows are disclosed, for example, in U.S. Pat. Nos. 2,744,487, 3,299,851, 3,837,226, and 4,245,566.

To provide for better illumination, Thomas Canty invented a light pipeline device as described in U.S. Pat. No. 4,746,178, which is incorporated by reference herein, for illuminating the interior of a pressure vessel. The device comprises a housing containing a fiber optic rod running from an external light source to a fused glass, laminated barrier disc. The unit is securely mounted on the vessel apart from a separate viewing window, with the barrier disc being arranged adjacent the interior of the vessel, whereby source light is transmitted to illuminate the vessel contents.

Combination illumination and camera viewing units are described, for example, in U.S. Pat. No. 5,230,556 to Canty et al., which is incorporated by reference herein. Units of this type include a centrally located camera for automatic viewing through a sight glass and a light guide delivering light through the sight glass adjacent the camera lens for illumination along an axis substantially parallel to the camera lens axis.

U.S. Patent Application Pub. No. 2003/0103756, which is incorporated by reference herein, describes an illumination module that provides illumination of a fluid at a point spaced inwardly from a viewing window. In addition, U.S. Pat. No. 6,450,655, which is also incorporated by reference herein, describes an illuminating and viewing unit for illuminating the interior of a vessel that includes an insertion assembly for allowing a camera lens and an illumination guide to extend into the interior of a vessel while being sealed off from the fluid in the vessel. In the system of the '655 patent, the camera is disposed exterior to the vessel, so that the deeper the insertion of the lens into the vessel interior, the longer the lens length. Longer lens lengths cannot provide the sharp focus that shorter lens length systems can provide, particularly when precise observations are desired, such as when observing tiny particles suspended in the fluid which require sharper images as those provided by short lens length cameras.

SUMMARY OF THE INVENTION

An object of the present invention is to provide an inspection device for inspecting a fluid in a vessel, in which a camera is insertable into the interior of the vessel. A further or alternate object of the present invention is to provide a inspection device suitable for a short lens length camera to provide high quality images of a fluid in the vessel and of particles within the fluid. A further or alternate object of the present invention is to provide improved lighting conditions for inspecting a fluid in a vessel. Another further or alternate object of the present invention is to provide an inspection device capable of inspecting fluids in a vessel that may be otherwise difficult to observe due to conditions such as high temperature, high pressure, volatility, toxicity, corrosiveness, etc. Yet another further or alternate object of the present invention is to overcome adverse thermal effects on a camera inserted into the interior of a vessel. Still another further or alternate object of the present invention is to provide a fluid inspection system capable of inspecting fluid in a gap between a lens and a light guide so that illumination is provided from behind the fluid at one or more angles.

The present invention provides a fluid inspection device for inspecting a fluid in a vessel that includes an elongate insertion well having a rear end disposed at the wall of the vessel and a front end disposed in the interior of the vessel. An inside of the insertion well is sealed off from the fluid in the vessel and an outside of the insertion well is in contact with the fluid in the vessel. The fluid inspection device also includes a camera unit disposed in the inside of the insertion well and a lens in operative communication with the camera unit and disposed at the front end of the insertion well so that a front end of the lens is in contact with the fluid and a rear end of the lens is inside the insertion well. The fluid inspection device also includes a light guide having a light emitting end and configured to guide light from the inside of the insertion well to the light emitting end. The light emitting end is disposed forward of the front end of the lens and directs the light at an angle toward the front end of the lens. A gap between the front end of the lens and the light emitting end is capable of receiving the fluid.

The insertion well that extends into the interior of the vessel provides a space that is sealed off from the fluid in the vessel so that the camera can be inserted into the interior of the vessel to observe the process, thus enabling use of a short lens system to obtain high image quality of the fluid. In addition, guiding light with a light guide to a point forward of the lens and directing the light at an angle toward the front of the lens provides excellent illumination for viewing and or imaging the fluid. In this manner, very high quality images of the fluid can be obtained so that characteristics of the fluid may be determined with a high degree of accuracy. For example, the color, turbidity, state (e.g. gas or liquid), and the general makeup of the fluid may be accurately determined. Moreover, the presence or absence of particles entrained in the fluid can be accurately observed and characteristics of such particles determined. For example, the size, shape, density, color, and surface of the particles may be accurately determined.

The fluid in the vessel may include a gas and or a liquid. The fluid may also include fluidized solids, such as a quantity of pellets suspended in a moving air current. The vessel may also contain a combination of one or more gases, liquids and solids. The angle at which the light is directed toward the front of the lens may advantageously be zero degrees so as to provide direct backlighting of the fluid. The angle may also be any angle from zero degrees up to nearly 90 degrees. Preferably, the angle is adjustable so that various lighting effects are available and an optimum illumination conditions can be obtained depending on the circumstances.

The inspection device may also include a light source that is mounted exterior to the vessel, and the light guide is configured to guide the light from the light source, through the inside of the insertion well, to the light emitting end. The type, color and/or intensity of the light may also be varied depending on the characteristics of the fluid or fluids being observed. As used herein, light includes both visible and non-visible forms of light and other forms of radiation.

Preferably, a relative position of the camera and the lens is adjustable, forward and backward within the insertion device to change a relative distance between the lens and the light emitting end of the light guide and, thus, to change a size of the gap. A dynamic seal is preferably provided between the lens and the front end of the insertion well that is capable of sealing off the inside of the insertion well during an adjustment of the relative position of the camera and the lens. The size of the gap may also be adjustable, alternatively or additionally, by changing a relative position of the light guide and light emitting end. Adjusting the size of the gap allows the user to optimize the conditions for inspecting the fluid depending on the qualities of the fluid or fluids and the desired characteristics to be inspected. For example, a high turbidity fluid, or one having a high concentration of particles may be more appropriately observed through a narrow gap so that the light may penetrate the fluid and/or particles. A low turbidity fluid and/or one having a lower concentration of particles may be better observed through a wider gap.

Preferably, the fluid inspection device includes a thermal insulation layer between the camera and a wall of the insertion well. A heat pipe may be provided to conduct heat from the inside of the insertion well to the exterior of the vessel, preferably to a heat exchanger. The heat pipe is preferably a thermally conductive metal, such as copper.

An actuator device may be disposed exterior to the vessel and configured to adjust the relative position of the camera and the lens forward and backward. A shaft disposed in operative connection with the actuator device and the camera unit may be used in adjusting the relative position of the camera and the lens.

The size of the gap may be any size and is preferably between 0.1 mm and 400 mm. The size and shape of the insertion well may vary depending on the size of the vessel and other factors. Typically, the insertion well will be cylindrical in shape and have a length of between 10 cm and 400 cm, and a diameter of between 1 cm and 40 cm.

The present invention also provides a method of inspecting a fluid in a vessel. The method includes the steps of: inserting an elongate insertion well having a front end into the interior of the vessel so that an inside of the insertion well is sealed off from the fluid; disposing a lens at the front end of the insertion well so that a front end of the lens is in contact with the fluid; disposing a camera unit inside of the insertion well and in operative connection with the lens; guiding light from inside the insertion well to a point forward of the lens so as to form a gap between the point and the lens and directing the light from the point to the lens; permitting the fluid to enter the gap; and capturing an image of the fluid in the gap.

In addition, the present invention provides a fluid inspection device for inspecting a fluid in a vessel, that includes: a camera disposed in an interior of the vessel, sealed off from the fluid, and in fluid communication with an exterior of the vessel; a lens in operative communication with the camera and in contact with the fluid; and a light guide for guiding light from the exterior of the vessel and having a light emitting end surface disposed in the interior of the vessel in contact with the fluid and facing toward the lens so as to define a gap for receiving the fluid between the lens and the light emitting end surface. The gap is preferably adjustable.

BRIEF DESCRIPTION OF THE DRAWINGS

The present invention is described in more detail below with reference to the drawings, in which.

DETAILED DESCRIPTION

Figure 1:
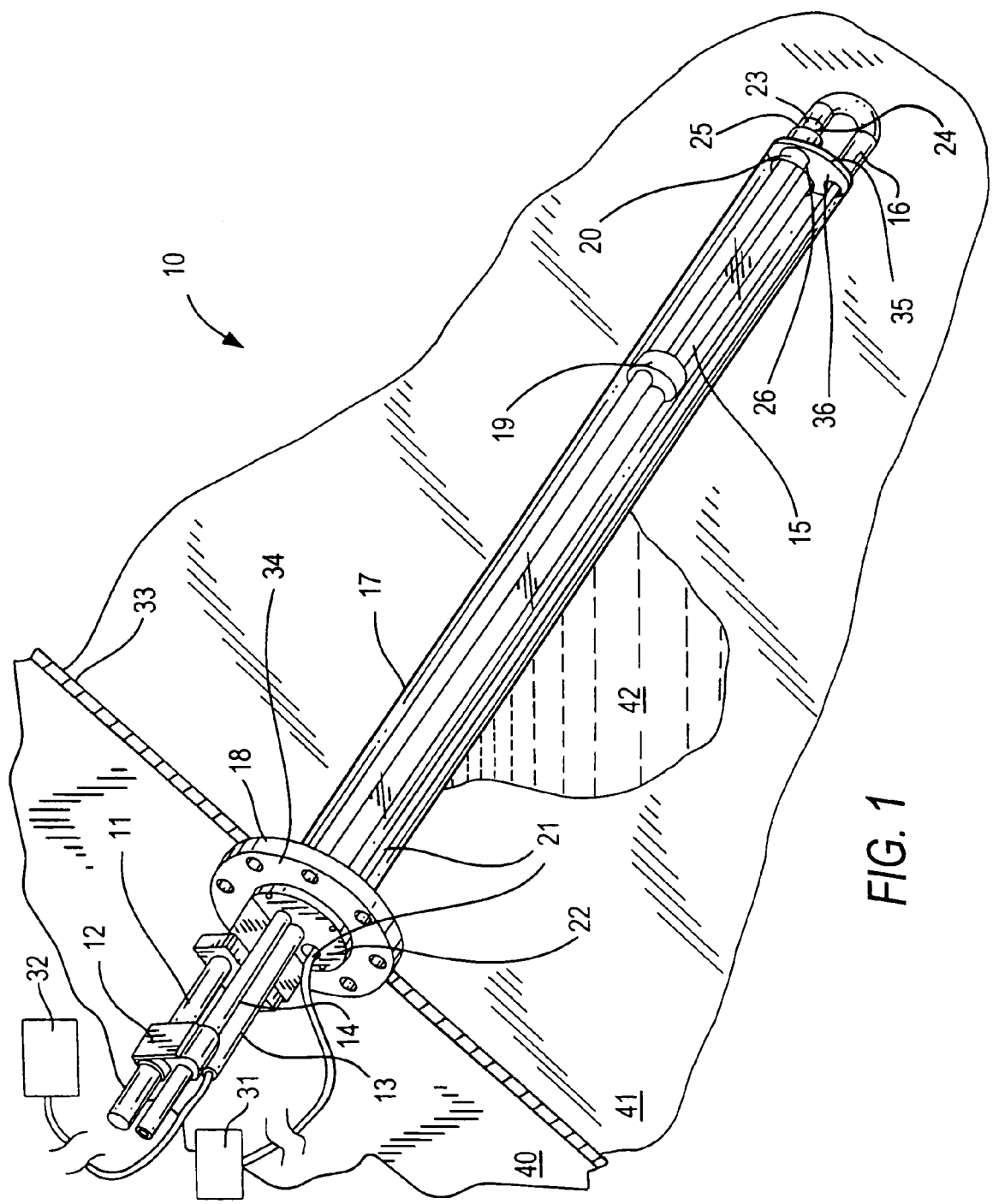
FIG. 1 shows a perspective view of the fluid inspection device according to the present invention.

In FIG. 1, fluid inspection device 10 includes an elongated insertion well 17 that extends from rear end 34 at a wall 33 of the vessel, to front end 35 located within the vessel interior 41. The insertion well 17 is cylindrical in shape and is mounted at the rear end 34 to the vessel wall 33 in a sealing manner using, for example, flange mount 18, so that the inside of the insertion well is sealed off from fluid 42 and the outside of insertion well 17 is in contact with fluid 42. An instrument support bracket 22 is mounted to the flange mount 18 and can be used to support various external instruments of the inspection device 10.

A camera unit 15 is disposed inside of the insertion well 17 and is sealed off from the fluid 42. A lens 20 is disposed at front end 35 and extends through front end 35 so that a front end 25 of the lens 20 is in contact with the fluid 42 and a rear end of the lens 20 is inside of the insertion well 17 and in operative communication with the camera unit 15. As used herein, camera and camera unit include devices that sense visible as well as non-visible light (e.g. infrared, near infrared, ultra violet, etc.) or other forms of radiation.

The front end 35 of cylindrical well 17 may include a front end cap 36, preferably made of a chemically resistant metal, such as stainless steel. The lens preferably includes a fused glass to metal construction to provide a pressure tight and corrosion resistant seal. A dynamic seal 26 between the front end cap 36 and lens 20 prevents fluid from entering into the inside of the insertion well 17, while allowing a relative movement in the longitudinal direction between front cap 36 and lens 20.

Light guide 21, which is preferably in the form of a fiber optic bundle, guides light from light source 31 disposed at an exterior 40 of the vessel, through insertion well 17. The light guide 21 also includes a light pipe 16 mounted on the front cap 36 and extending to light emitting end 23 at a point forward of the front end 25 of lens 20. A purpose of the light pipe 16 is to guide the light to a point forward of the lens and to direct the light toward the end so as to illuminate the fluid in front of the lens 20 and improve the quality of images of the fluid taken by the camera unit 15. In the embodiment shown in FIG. 1, light pipe 16 includes a u-shaped portion so that the light guide is bent back 180 degrees and the light emitting end is directly facing the front end 25 of lens 20, forming gap 24 in between, so that the light is directed at an angle of 0 degrees toward the lens 20. It is also envisaged that the light pipe 16 could have different shapes so that the light is directed at an angle to the lens. Depending on several factors, such as the purpose of the inspection and the qualities of the fluid, it may be desirable to direct the light at an angle anywhere from 0 degrees for direct backlighting of the fluid to almost 90 degrees for predominantly side lighting. In addition, a plurality of light guides may be used to provide a combination of lighting effects on the fluid in the gap 24. The gap 24 is defined herein as the space between light emitting end 23 and the front end 25 of lens 20, and a size of the gap is the nearest distance from the lens front end 25 to the light emitting end 23. The light pipe 16 may be rigid to provide a permanent shape, or may be flexible for adjusting the angle of the light toward the lens.

A back cap 19 is disposed at the rear of camera unit 15. A heat pipe 13 extends from back cap 19 to the exterior 40 of the vessel 33 and may connect to a heat exchanger 32. Both back cap 19 and heat pipe 13 are preferably made of a thermally conductive metal such as copper. In applications in which the fluid 42 in the interior 41 of the vessel is hot, heat is absorbed through the walls and frond end of the insertion well 17 and through lens 20. To avoid excessive heat that may impede the functioning of the camera, heat is conducted away from the camera unit 15 through back cap 19 and led out to the exterior 40 of the vessel 33 via heat pipe 13, where it may be convected away to the ambient atmosphere at heat exchanger 32.

Conduit shaft 14 passes through back cap 19 and houses the electrical wiring to the camera unit 15. Conduit shaft 14 also provides a rigid connection to camera unit 15 so that a movement of the conduit shaft forward or backward within the insertion well 17 moves the entire camera unit 15 forward and backward within the insertion well 17. Lens 20 is also mounted rigidly to camera unit 15 so that the lens 20 also moves backward and forward with the camera unit and a size of the gap 24 is adjusted. Dynamic seal 26 between lens 20 and front cap 36 enables the relevant movement of the lens while maintaining a tight seal and preventing fluid from entering the insertion well 17. An actuator 11 mounted on the instrument support bracket 22 on the exterior 40 of the vessel wall 33 is used to adjust the forward and rearward position of the camera unit 15 and the lens 20. An adapter bracket 12 connects the actuator 11 to the conduit shaft 14.

Figure 2:
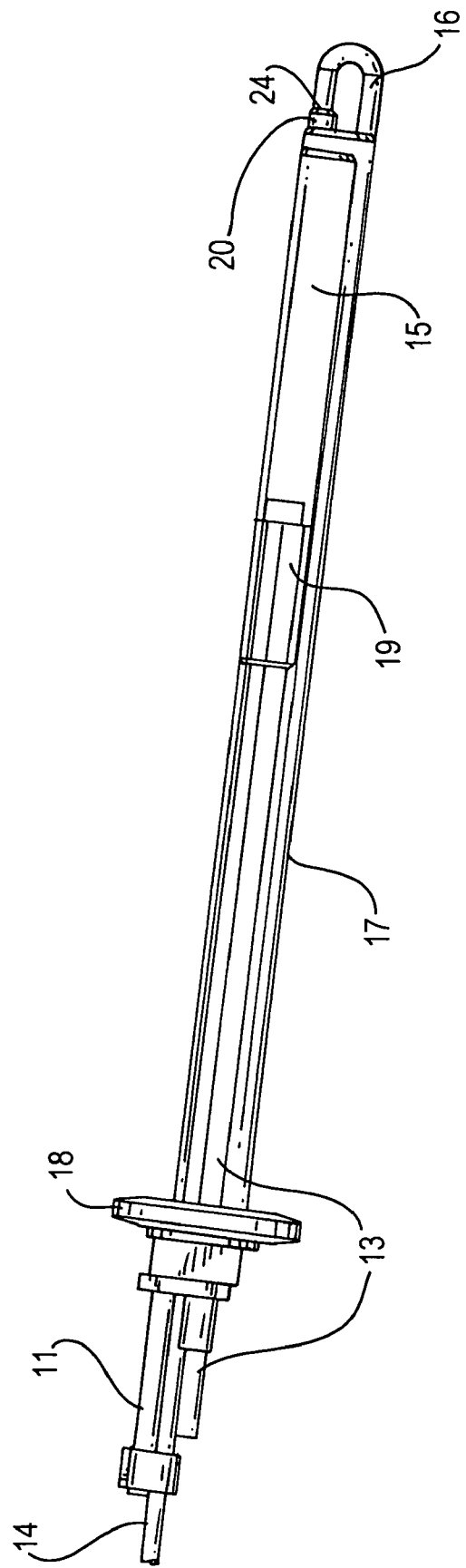
FIG. 2 shows a side schematic view of a second embodiment of a fluid inspection device.

FIG. 2 shows a schematic side view of a second embodiment of the fluid inspection device of the present invention. In FIG. 2, similar elements are numbered using the same reference numbers. The embodiment of FIG. 2 differs from the previous embodiment in that the camera back cap 19 is enlarged so as to provide better heat dissipation properties. Preferably back cap or heat sink 19 is made of a thermally conductive metal. The larger mass of the back cap 19 in FIG. 2 enables it to store more heat and more effectively conduct the heat away from the camera unit and to heat pipe 13.

Figure 3:
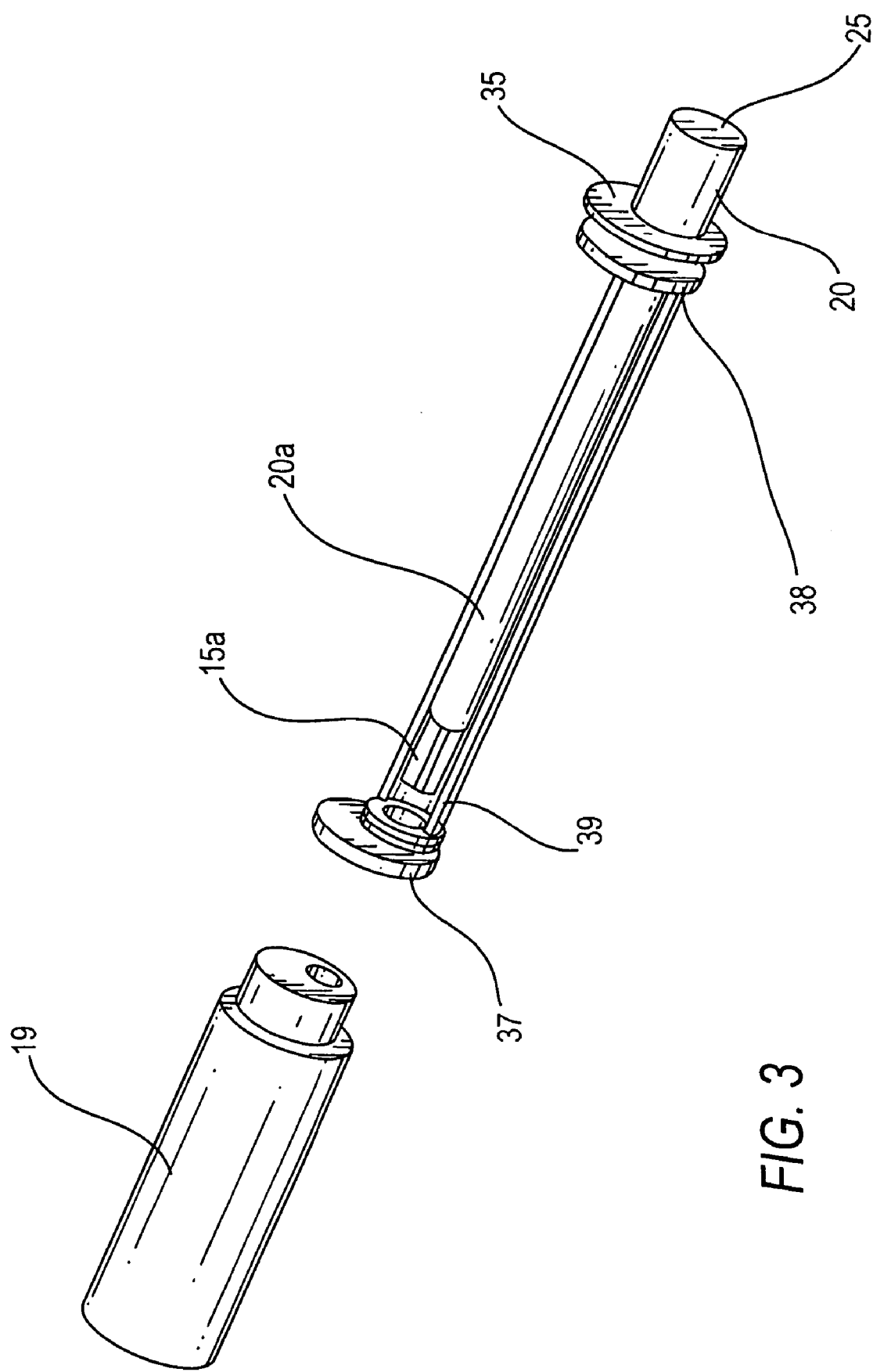
FIG. 3 shows a perspective schematic view of several components of the fluid inspection device of FIG. 2.

FIG. 3 provides a view of some of the internal components of the fluid inspection device. Camera 15a, which is preferably a high resolution CCD camera is shown within camera unit 15. Also, lens element 20a, which is in operative connection with lens 20 is also shown. Camera lens support bracket 39 extends from mounting bracket 37 at the rear of the camera unit 15 along lens element 20a to lens 20 to provide support and rigidity between the camera unit 15 and the lens 20 so that, when the camera unit 15 is adjusted using a actuator 11 and shaft 14, the lens 20 moves along with the camera unit 15. Insulation cap 38 thermally insulates camera unit 15 from heat that might flow from the fluid through the front cap 36 of the insertion well 17. Preferably, a layer of insulation is also provided around the circumference of the camera unit 15 within the insertion well 17, as well as around the lens 15a and camera 20a.

What is claimed is:

1. A fluid inspection device for inspecting a fluid in a vessel, the fluid inspection device comprising:
   an elongate insertion well having a rear end disposed at the wall of the vessel and a front end disposed in the interior of the vessel, an inside of the insertion well being sealed off from the fluid in the vessel and an outside of the insertion well being in contact with the fluid in the vessel;
   a camera unit disposed in the inside of the insertion well;
   a lens in operative communication with the camera unit and disposed at the front end of the insertion well so that a front end of the lens is in contact with the fluid and a rear end of the lens is inside the insertion well; and
   a light guide having a light emitting end and configured to guide light from the inside of the insertion well to the light emitting end, the light emitting end being disposed forward of the front end of the lens and directing the light at an angle toward the front end of the lens, a gap between the front end of the lens and the light emitting end capable of receiving the fluid.

2. The fluid inspection device as recited in claim 1, wherein the angle is 0 degrees for direct backlighting.

3. The fluid inspection device as recited in claim 1, wherein the angle is adjustable.

4. The fluid inspection device as recited in claim 1, wherein the fluid is one of a gas, a liquid, and fluidized solids.

5. The fluid inspection device as recited in claim 1, wherein the vessel contains a gaseous fluid and a liquid fluid.

6. The fluid inspection device as recited in claim 1, further comprising a light source disposed exterior to the vessel and wherein the light guide is configured to guide light from the light source, through the inside of the insertion well, to the light emitting end.

7. The fluid inspection device as recited in claim 1, wherein a relative position of the camera and the lens is adjustable so as to change a size of the gap.

8. The fluid inspection device as recited in claim 7, further comprising a dynamic seal between the lens and the front end of the insertion well and capable of sealing off the inside of the insertion well during an adjustment of the relative position of the camera and the lens.

9. The fluid inspection device as recited in claim 1, wherein a relative position of the light emitting end is adjustable so as to change a size of the gap.

10. The fluid inspection device as recited in claim 1, further comprising a thermal insulation layer between the camera and a wall of the insertion well.

11. The fluid inspection device as recited in claim 1, further comprising a heat pipe configured to conduct heat from the inside of the insertion well to the exterior of the vessel.

12. The fluid inspection device as recited in claim 11, further comprising a heat exchanger disposed exterior of the vessel and in operative connection with the heat pipe.

13. The fluid inspection device as recited in claim 11, wherein the heat pipe includes a conductive metal.

14. The fluid inspection device as recited in claim 7, further comprising an actuator device disposed exterior to the vessel and configured to adjust the relative position of the camera and the lens forward and backward.

15. The fluid inspection device as recited in claim 14, further comprising a shaft disposed in operative connection with the actuator device and the camera unit for use in adjusting the relative position of the camera and the lens.

16. The fluid inspection device as recited in claim 1, wherein a size of the gap is between 0.1 mm and 400 mm.

17. The fluid inspection device as recited in claim 16, wherein a length of the insertion well is between 10 and 200 cm.

18. The fluid inspection device as recited in claim 1, wherein the insertion well is cylindrical in shape.

19. The fluid inspection device as recited in claim 18, wherein a diameter of the insertion well is between 1 and 40 cm.

20. A method of inspecting a fluid in a vessel, the method comprising:

inserting an elongate insertion well having a front end into the interior of the vessel so that an inside of the insertion well is sealed off from the fluid;

disposing a lens at the front end of the insertion well so that a front end of the lens is in contact with the fluid;

disposing a camera unit inside of the insertion well and in operative connection with the lens;

guiding light using a light guide from inside the insertion well to a point forward of the lens so as to form a gap between the point and the lens and directing the light from the light guide toward the lens;

permitting the fluid to enter the gap; and capturing an image of the fluid in the gap.

21. A fluid inspection device for inspecting a fluid in a vessel, the fluid inspection device comprising:

a camera disposed in an interior of the vessel, sealed off from the fluid, and in fluid communication with an exterior of the vessel;

a lens in operative communication with the camera and in contact with the fluid; and a light guide for guiding light from the exterior of the vessel and having a light emitting end surface disposed in the interior of the vessel in contact with the fluid and facing toward the lens so as to define a gap for receiving the fluid between the lens and the light emitting end surface.

22. The fluid inspection device as recited in claim 19, wherein the gap is adjustable.

* * * * *